United States Patent [19]

Stark

[11] 4,091,992
[45] May 30, 1978

[54] PNEUMATIC PRESSURE TRANSMITTER RESPONSIVE TO TEMPERATURE AND HUMIDITY

[75] Inventor: Ernest H. Stark, Rockford, Ill.

[73] Assignee: Barber-Colman Company, Rockford, Ill.

[21] Appl. No.: 790,372

[22] Filed: Apr. 25, 1977

[51] Int. Cl.² .................................. G05D 22/00
[52] U.S. Cl. .................... 236/44 C; 73/336; 236/87; 200/61.06
[58] Field of Search ............ 236/87, 44 C, 99 A, 236/101 E, 101 R; 200/61.06; 73/336; 62/176 E

[56] References Cited

U.S. PATENT DOCUMENTS

| | | | |
|---|---|---|---|
| 3,970,246 | 7/1976 | Attridge, Jr. et al. | 200/61.06 |
| 3,999,706 | 12/1976 | Lewis | 236/44 C |

*Primary Examiner*—William E. Wayner
*Attorney, Agent, or Firm*—Robert M. Hammes, Jr.

[57] ABSTRACT

A force-balance transmitter for producing a pressure signal proportional to the enthalpy of air has a flapper associated with a nozzle and employs a control force acting on the flapper in opposition to a feedback force applied to the flapper by the controlled fluid pressure acting over the area of the nozzle, the control force being produced by the combination of forces exerted on the flapper by two resilient beams subjected to individual bending moments responsive to sensed temperature and sensed humidity respectively.

19 Claims, 4 Drawing Figures

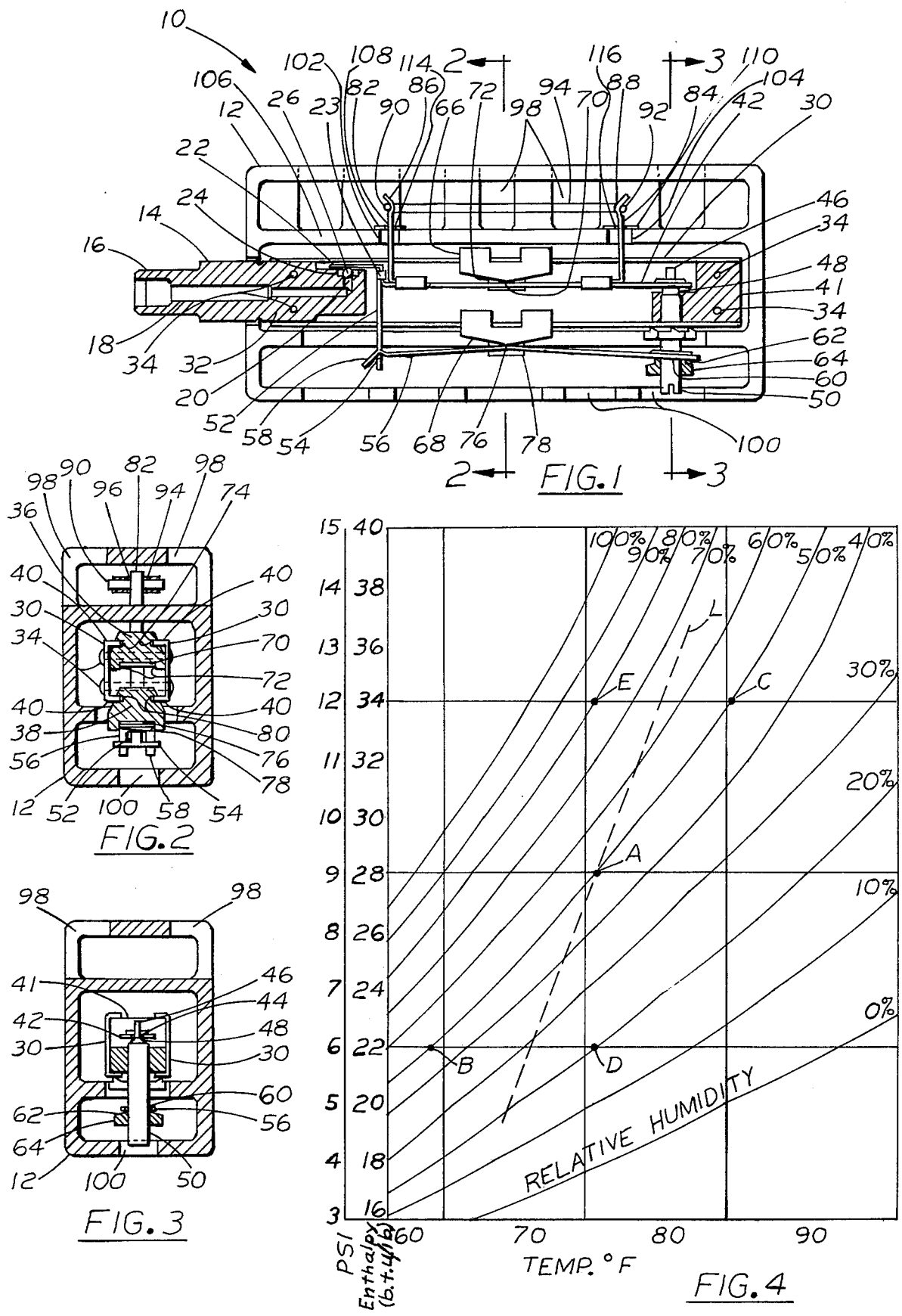

PNEUMATIC PRESSURE TRANSMITTER RESPONSIVE TO TEMPERATURE AND HUMIDITY

BACKGROUND OF THE INVENTION

This invention relates to pneumatic devices which transmit a pressure signal in response to a sensed condition. More particularly, it relates to a force-balance pressure transmitter which produces a signal in response to the combined effect of sensed temperature and humidity.

Force-balanced pressure transmitters are well-known and operate by balancing a force proportional to the controlled pressure of the fluid against a control force generated by a condition being sensed. Such force-balance transmitters are thus distinguished from position-sensitive devices in which the measured condition is converted into a variable, relatively inflexible position of a means controlling fluid pressure. The force due to the controlled pressure constitutes a negative feedback that tends to linearize the relationship of the fluid pressure to the variable measured condition. In a typical pressure transmitter, a nozzle and flapper may be employed in a manner such that a control force exerted by the flapper in response to a sensed condition is exposed by a feedback force due to the fluid pressure acting over the area of the nozzle. Such a transmitter is described in my U.S. Pat. No. 3,452,928.

In certain applications it is desirable to determine the total heat or enthalpy of a fluid. For example, in a comfort conditioning system it is typical to utilize outside air to a certain extent in providing properly conditioned air for distribution to various zones. For purposes of energy conservation it is important to determine how much outside air should be used to minimize energy consumption. The energy required to condition air is proportional to the enthalpy of the air. Thus, by comparing the enthalpy of the outside air to that of the return air in the conditioning system a determination can be made as to the amounts of outside air and return air which should be used to accomplish the desired conservation of energy. The enthalpy of air is the sum of the enthalpy of the dry air plus the enthalpy of the moisture present in the air. The enthalpy of dry air is proportional to the temperature of the air and this enthalpy can be determined by utilizing a temperature sensor. The enthalpy of the moisture in the air is proportional to humidity. Thus the moisture enthalpy can be determined by utilization of a humidity sensor. Consequently, it is necessary to combine the outputs of the temperature and humidity sensors to obtain a control signal proportional to the enthalpy of the moist air.

Another application in which it is desirable to employ a transmitter which combines sensed temperature and sensed humidity is in the determination of the dew point of air. In a given zone it may be critical to prevent condensation which could damage the contents in the zone and thus it would be important to maintain the temperature above the dew point. The dew point depends on the temperature and relative humidity of the air. Properly combining the outputs of temperature and humidity sensors will result in a signal indicative of the dew point.

SUMMARY OF THE INVENTION

According to the invention disclosed a force-balance pneumatic pressure transmitter produces a pressure signal which varies as a function of both temperature and humidity. A flapper exerts a control force which is opposed by the force resulting from the controlled pressure acting over the area of an associated nozzle. Temperature responsive means and humidity responsive means apply bending moments to respective resilient beams which are associated with the flapper. As a result of the applied bending moments each beam exerts a force on the flapper dependent on sensed temperature or humidity changes. These two forces are summed and the control force exerted by the flapper is thus dependent on both temperature and humidity. Rate adjusting means is provided so that proper relationships between temperature and humidity can be obtained so as to provide a pressure signal indicative of the enthalpy or of the dew point of the air.

The invention provides a transmitter having good linearity over its sensing range. The construction permits simple but accurate adjustment of the relationship between temperature and humidity. Other features and advantages will become apparent from the following detailed description taken in conjunction with the drawings.

BRIEF DESCRIPTION OF THE DRAWINGS

FIG. 1 is a sectional view of a pneumatic pressure transmitter responsive to both temperature and humidity.

FIG. 2 is a sectional view taken along line 2—2 of FIG. 1.

FIG. 3 is a sectional view taken along line 3—3 of FIG. 1.

FIG. 4 is a graphical representation of the relationships between temperature, humidity, enthalpy and the pressure signal.

DESCRIPTION OF THE PREFERRED EMBODIMENT

A force balance pneumatic pressure transmitter 10, as shown in FIG. 1, has a housing 12 which carries a fitting 14 adapted to be connected at end 16 to a restricted supply of fluid under pressure. Fitting 14 has a passageway 18 which permits pressurized fluid to flow to nozzle 20 located inside housing 12. A flapper 22 is provided which is operatively associated with nozzle 20 so as to vary the flow through the nozzle. Around the nozzle 20 is a counterbore 24 which acts as a cage for a small, light ball 26 positioned between flapper 22 and nozzle 20 to insure proper closure of the nozzle in spite of any mismatch between flapper 22 and nozzle 20. In the force-balance transmitter disclosed, a control force is exerted by flapper 22 in opposition to a feedback force resulting from the pressurized fluid acting over the area of nozzle 20. When these two forces are in equilibrium the transmitted pressure signal is constant at a value corresponding to a sensed condition. The nozzle area is relatively large so that the resulting force is of a magnitude equal to that of the control force exerted by flapper 22. This is distinguished from a position sensitive device in which the nozzle area is small and the control force exerted by the flapper is much greater in magnitude and relatively independent of the force exerted against the flapper by the pressurized fluid. In transmitter 10 the motion required of ball 26 to change the pressure signal from minimum to maximum (typically, 3 to 15 p.s.i.) is very small (on the order of 0.0005 inch) so that the motion required of flapper 22 is negligible and the transmitter is almost completely force-balanced in operation.

A pair of opposed elongated channels 30, best seen in FIG. 2, are attached at one end to mounting portion 32 of fitting 14 by any suitable means such as rivets 34 thus forming a tubular section having upper and lower slots 36, 38 formed by opposing flanges 40. Channels 30 are attached at their other ends by mounting block 41 in a similar manner, as with rivets 34.

A resilient beam 42 is joined at one end to flapper 22 by connection 23 and is provided with a hole 44 at the other end which fits over post 46 and against shoulder 48 permitting beam 42 to pivot thereon (shown in FIGS. 1 and 3). Both post 46 and shoulder 48 are part of set point adjusting screw 50. It will be apparent that flapper 22 may also be an integral part of beam 42. Depending from connection 23 is a vertical connecting member 52 having a cross member 54, best seen in FIG. 2. A second resilient beam 56 substantially parallel to said first beam is supported at one end by means of a notched portion 58 which fits around member 52 and over cross member 54. Beam 56 is provided with a hole 60 at its other end which fits over screw 50 and against shoulder 62 of adjustable nut 64.

Biasing bending moments are applied to resilient beams 42, 56 by means of adjustable abutments such as sliders 66, 68 respectively. Slider 66 contacts beam 42 along knife edge 70 between walls 72 which limit lateral motion of the beam. A pair of oppositely facing grooves 74 on slider 66 engage a pair of the opposed flanges 40 which serve as guides establishing a path for movement of slider 66 along the length of beam 42. Slider 66 engages beam 42 on the side opposite to shoulder 48 and between flapper 22 and post 46. Similarly, slider 68 contacts resilient beam 56 along knife edge 76 between walls 78 which limit lateral motion of the beam. Grooves 80 engage a pair of opposed flanges 40 to establish a path for guiding movement of slider 68 along the length of beam 56. Slider 68 engages beam 56 on the side opposite to and between shoulder 62 and cross member 54.

It is thus seen that flapper 22, resilient beam 42 and resilient beam 56 are interconnected so that independent forces which may be exerted by beams 42, 56 due to bending moments applied result in a single control force exerted by flapper 22 in opposition to the force created by the fluid pressure acting over the area of nozzle 20.

The control force exerted by flapper 22 is made dependent on the combined effects of sensed humidity and sensed temperature by applying to one of beams 42, 56 a variable bending moment responsive to temperature and to the other beam a variable bending moment responsive to humidity. In the following exemplary description the bending moment applied to resilient beam 42 is humidity dependent and that applied to resilient beam 56 is temperature dependent.

A pair of members 82, 84 are rigidly fixed perpendicular to beam 42 and are preferably proximate to respective ends of the beam. Members 82, 84 are formed to provide respective retaining portions 86, 88 for respective pins 90, 92 holding in tension between them a condition sensitive element in the form of a closed loop 94. This sensitive element could be made of material which is responsive to temperature or humidity, but in the following description loop 94 is made of nylon or other material which expands and contracts with changes in humidity. Holes 96 are provided in loop 94 where it passes around pins 90, 92 to provide a clearance for member 82, 84. Openings 98 are in the upper portion of housing 12 to permit circulation of the conditioned air around the humidity responsive loop 94. Since nylon expands in response to an increase in humidity and contracts in response to a decrease in humidity, a bending moment responsive to humidity changes is applied to beam 42 through vertical members 82, 84. As evident from beam theory, the biasing bending moment and the humidity responsive bending moment cause a humidity dependent control force to be exerted by flapper 22 in opposition to the fluid pressure at the nozzle 20 since flapper 22 is connected to beam 42.

Resilient beam 56 is shown as a laminated composite material in which the laminations are made of materials having different coefficients of expansion. A bending moment is created by the differential expansion and contraction of the laminations in response to a sensed condition. Beam 56 could be either temperature or humidity responsive, but as described below it is responsive to temperature. Free circulation of air around beam 56 is provided by means of openings 100 in the bottom of housing 12.

In order to obtain the temperature responsive bending moment, resilient beam 56 is a thermostatic bimetal. When a bimetal is unrestrained, a change in temperature manifests itself as movement and when it is restrained a variable bending moment results so that temperature changes are manifested as a variable force applied to its restraints. Since beam 56 is restrained by shoulder 62, slider 68 and cross member 54 sensed temperature changes result in a temperature dependent control force being exerted on cross member 54 due to the biasing bending moment and the temperature responsive bending moment. Since connecting member 52 is fixed to flapper 22 so that it exerts a temperature dependent control force in opposition to the fluid pressure at nozzle 20, the total force exerted by flapper 22 is dependent on both temperature changes and humidity changes.

As previously noted, in a device which combines the effects of sensed temperature and humidity into a control signal indicative of a condition of air such as enthalpy or dew point it is essential to obtain the proper relationship between the temperature and humidity signals. Psychrometric charts are available which give graphic representations of the properties of a mixture of air and water vapor. For instance, at a given dry bulb temperature and relative humidity it is possible to determine the enthalpy of the air-vapor mixture and the dew point. The bending moment applied to resilient beam 42 results in a control force component indicative of humidity and that applied to beam 56 results in a component indicative of dry bulb temperature. In using transmitter 10 as an enthalpy transmitter and assuming a constant relative humidity, fluctuations in temperature must result in a pressure signal corresponding to the enthalpy values which are obtained from the psychrometric chart for such temperature fluctuations. Similar principals apply when relative humidity varies at a constant temperature.

A principal advantage of the invention is that movable sliders 66, 68 provide a rate adjusting means which permits attainment of the proper pressure signal span for a given sensed condition span. In order to obtain the proper relationship between temperature and humidity sliders 66, 68 may be moved along the lengths of resilient beams 42, 56 respectively to the proper position. As apparent from beam theory the movement of sliders 66, 68 results in a change in the forces exerted by flapper 22.

As sliders 66, 68 are moved toward flapper 22 the force exerted by the flapper on ball 26 increases and the change in force resulting from changes in the bending moments applied to beams 41, 56 due to sensed changes in humidity and temperature will be greater. The change in sensed condition required to shift the control signal pressure by a specified amount is therefore less.

FIG. 4 shows a graphical representation of the relationship between dry bulb temperature, relative humidity and enthalpy similar to a psychrometric chart. Temperature of ° F is plotted along the abscissa and enthalpy in btu/lb is plotted along the ordinate. The temperature and enthalpy ranges shown are typical of those encountered in a comfort conditioning system. A control pressure scale, shown as ranging from 3 to 15 p.s.i. and corresponding to the enthalpy value sensed by transmitter 10, is also plotted along the ordinate. Lines of constant relative humidity are also shown. Sliders 66, 68 must be positioned so that the pressure signal produced at a given temperature and humidity corresponds to that shown in FIG. 4.

In order to properly calibrate transmitter 10 it is necessary to adjust the positions of sliders 66, 68 so that the proper relationship is obtained between the control force components due to sensed temperature and sensed humidity. The calibration is described for a transmitter which is used as an enthalpy sensor but it will be apparent that the principles also apply when the transmitter is to be used to sense dew point or some other condition dependent on the combination of humidity and temperature.

Typical ranges of temperature, enthalpy and humidity encountered in a comfort conditioning application are those shown in FIG. 4. The pressure signal scale is set up so that a pressure signal span typical of pneumatic systems (3 to 15 p.s.i.) corresponds to the enthalpy span likely to exist in a controlled zone.

Transmitter 10 is located in a controlled zone in which temperature and humidity can be varied. Initially, the condition of the air is held at an appropriate temperature and humidity set point such as set point A on FIG. 4 corresponding to 50% relative humidity and approximately 75° F. Initially, sliders 66, 68 are preferably located approximately midway between flapper 22 and screw 50. The positions of shoulder 48 and nut 64 must be independently set to obtain the proper temperature and humidity contributions to the desired pressure signal (approximately 9 p.s.i.) at set point A. From FIG. 4 it is seen that at a constant temperature of approximately 75° F the pressure signal component due to humidity is approximately 5 p.s.i. since an increase in humidity from 0 to 50% results in a desired pressure signal change from approximately 4 p.s.i. to approximately 9 p.s.i. To obtain the proper setting for shoulder 48 the notched end of beam 58 is disengaged from connecting number 52 so that the pressure signal is dependent only on sensed humidity. Screw 50 is then adjusted until the pressure signal is at 5 p.s.i. Beam 56 is them released to engage connecting member 52 so that the signal has both humidity and temperature components. The proper pressure signal component due to temperature is now obtained by adjusting the postion of nut 64 until the combined pressure signal is 9 p.s.i. (corresponding to 75° F and 50% relative humidity in FIG. 4).

Once the set point is obtained span adjustment can be made to obtain the proper proportional span for sensed humidity and temperature by moving sliders 66, 68. To properly position slider 68 with respect to temperature sensitive beam 56, the relative humidity in the zone is held constant at 50%. Calibration points B (63° F, 6 p.s.i.) and C (84.5° F, 12 p.s.i.) are chosen on the 50% constant relative humidity line. The temperature is then allowed to vary over a given range (e.g. 60° F - 85° F). When slider 68 is properly positioned the pressure signal should vary from 6 p.s.i. to 12 p.s.i. when the sensed temperature varies from 63° F to 84.5° F. If slider 68 is, for example, too close to the notched end of beam 56 a given change in sensed temperature will result in a greater than desired change in the control force, and correspondingly a greater than desired change in the pressure signal. Graphically, this improper relationship between temperature change and pressure signal change might be represented by line L in FIG. 4. It is desired that with respect to sensed temperature the slope of line L approximate that of the 50% relative humidity line so that the pressure signal span for a given span of sensed temperature corresponds substantially to that shown in FIG. 4. This is accomplished by moving slider 68 further away from the notched end of beam 56 so that the change in control force for a given temperature change is not as great.

A similar procedure is used to properly position slider 66 with respect to resilient beam 42. In this instance the temperature in the zone is held constant at approximately 75° F and the humidity is allowed to vary over an appropriate range such as 10 to 90%. Calibration points D (20% relative humidity, 6 p.s.i.) and E (80% relative humidty, 12 p.s.i.) are chosen on the constant 75° F line. When the sensed humidity varies from 20 to 80% the pressure signal should vary from 6 p.s.i. to 12 p.s.i. If, for example, slider 66 is too close to flapper 22 a sensed humidity change will result in a greater than desired change in the control force, and correspondingly a greater than desired change in the pressure signal. Such an improper relationship might be represented by line L in FIG. 4. To obtain the proper relationship between sensed humidity and the pressure signal it is desired that with respect to humidity the slope of line L approximate that of the constant 75° F line. Moving slider 66 farther away from flapper 22 results in a smaller change in control force, and consequently in the pressure signal, for a given humidity change. Slider 66 is thus moved until the pressure signal changes from 6 p.s.i. to 12 p.s.i. when sensed humidity varies from 20 to 80%. Following adjustment of the positions of sliders 66, 68 it may be necessary to repeat the procedure for obtaining the proper set point by adjusting screw 50 and nut 64.

Once transmitter 10 is properly calibrated by set point adjustment and by span adjustment, the control force components produced by the humidity and temperature sensors are in proper relationship to each other to provide a total control force proportional to enthalpy. The span adjustment feature provided by sliders 66, 68 makes calibration relatively simple and accurate.

There is an additional factor, not previously discussed, which may affect the operational accuracy of transmitter 10. Since in a pneumatic system the air from nozzle 20 may have different temperature and/or humidity characteristics from that in the conditioned zone, permitting this air to freely circulate within housing 12 may result in inaccurate sensing of the humidity and/or temperature of the air in the conditioned zone. Transmitter 10 is thus preferably provided with means to limit the free circulation of air in housing 12 so as to shield the condition sensitive elements from air flowing from nozzle 20. An example of such means is shown in FIG. 1 with respect to condition sensitive loop 94. Members 82, 84 extend through holes 102, 104 in rib 106 of housing 12 which substantially isolates loop 94 from nozzle 20. To some degree, rib 106 limits the amount of nozzle air which circulates in the vicinity of loop 94. However, it is still possible for a certain amount of nozzle air to pass through holes 102, 104. In order to substantially eliminate the flow of air through holes 102, 104, an additional shielding means, such as circular discs 108, 110, may be provided. Discs 108, 110 rest on top surface 112 of rib 106 so as to cover holes 102, 104 respectively. Disc 108, 110 are provided with respective centrally located openings 114, 116 to permit members 82, 84 to extend therethrough. Openings 114, 116 are preferably sized to provide a minimum clearance around members 82, 84 so that air flow through holes 102, 104 is substantially eliminated while still permitting a degree of vertical movement of members 82, 84 with respect to discs 108, 110. In order to hold discs 108, 110 in contact with surface 112 a film of oil or other lubricant may be provided between the discs and surface 112. The resulting adhesive forces will prevent vertical movement of discs 108, 110 with respect to rib 106 while at the same time permitting movement in the horizontal plane as may be necessary in connection with movement of members 82, 84.

It will be readily apparent to those skilled in the art that many modifications are possible without departing from the scope and spirit of the invention. The embodiment described is exemplary only and thus the invention is limited solely by the claims.

I claim:

1. A force-balance pneumatic pressure transmitter responsive to temperature and humidity comprising:
   a nozzle;
   an inlet for conducting a restricted supply of fluid under pressure to said nozzle;
   a flapper operatively associated with said nozzle to vary fluid flow through the nozzle;
   a first pivot displaced from said nozzle;
   a first elongated resilient simple beam supported at one end upon said first pivot and connected at the other end to said flapper;
   a first abutment associated with said first beam and located between said nozzle and said first pivot biasing said flapper toward said nozzle through said first beam;
   a second pivot displaced from said nozzle;
   a second elongated resilient simple beam supported at one end upon said second pivot and connected at its other end to said flapper;
   a second abutment associated with said second beam and located between said nozzle and said second pivot biasing said flapper toward said nozzle through said second beam;
   first means for applying a bending moment to one of said beams in response to sensed temperature;
   second means for applying a bending moment to the other of said beams in response to sensed humidity, said first and second means acting together to apply a variable control force through said first and second beams to said flapper to modulate said fluid pressure in response to the sensed temperature and humidity, said fluid pressure acting over the area of the nozzle to provide to the flapper a negative feedback force proportional to said fluid pressure.

2. A transmitter according to claim 1 wherein one of said pivots is movable substantially perpendicular to a respective one of said beams.

3. A transmitter according to claim 2 wherein said one pivot comprises a post movable longitudinally.

4. A transmitter according to claim 3 wherein said post comprises a threaded portion and the other of said pivots comprises a nut threaded upon said threaded portion.

5. A transmitter according to claim 4 wherein said nut comprises a sloping shoulder in engagement with the other of said beams.

6. A transmitter according to claim 3 wherein said post comprises a sloping shoulder in engagement with said one beam.

7. A transmitter according to claim 1 wherein one of said abutments is movable along the length of its associated beam to permit span adjustment of the control force due to the bending moment applied by one of said first and second means.

8. A transmitter according to claim 1 wherein said second beam is connected to said flapper through a connecting member associated with said first beam.

9. A transmitter according to claim 8 wherein said first and second beams are substantially parallel to the plane of said flapper, said connecting member extending between the ends of said beams proximate to said flapper.

10. A transmitter according to claim 9 wherein said connecting member is rigidly fixed to said first beam.

11. A transmitter according to claim 10 wherein said second beam is detachable from said connecting member.

12. A transmitter according to claim 11 wherein said connecting member extends substantially perpendicular from said first beam and comprises a cross-member displaced from said first beam, said second beam having a notched end adapted to operatively engage said cross-member.

13. A transmitter according to claim 1 wherein said flapper and said first beam are one.

14. A transmitter according to claim 1 wherein one of said beams comprises a laminated composite material, the bending moment resulting from differential expansion and contraction of the laminations in response to change in one of the sensed temperature and the sensed humidity.

15. A transmitter according to claim 14 wherein said laminated composite material comprises a temperature responsive bimetal member.

16. A transmitter according to claim 1 wherein one of said first and second means comprises a pair of brackets displaced from each other and fixed substantially perpendicular to a respective beam, an element mounted between the free ends of said brackets, the bending moment resulting from expansion and contraction of said element in response to change in one of the sensed temperature and the sensed humidity.

17. A transmitter according to claim 1 additionally comprising means to shield one of said first and second means from fluid flowing from said nozzle.

18. A transmitter according to claim 16 additionally comprising a housing associated with said nozzle and said one means, said housing having a rib separating said element from said nozzle so as to inhibit the circulation of fluid from said nozzle around said element.

19. A transmitter according to claim 8 wherein said brackets extend from said respective beam through respective holes in said rib to said element, said transmitter additionally comprising a disc to cover one of said holes, said disc provided with an opening to permit a respective one of said brackets to extend therethrough.

* * * * *